(12) United States Patent
Ryu et al.

(10) Patent No.: US 6,869,602 B2
(45) Date of Patent: Mar. 22, 2005

(54) **METHOD FOR TREATING, PREVENTING, OR INHIBITING ENTEROTOXIGENIC *ESCHERICHIA COLI* INFECTIONS WITH BOVINE RED BLOOD CELLS**

(75) Inventors: Hyoik Ryu, Daegu (KR); Frederick J. Cassels, Ellicott City, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 214 days.

(21) Appl. No.: 10/077,804

(22) Filed: Feb. 20, 2002

(65) Prior Publication Data

US 2003/0157080 A1 Aug. 21, 2003

(51) Int. Cl.[7] .......................... A01N 1/02; A01N 63/00; A01N 65/00
(52) U.S. Cl. ................. 424/93.73; 424/93.4; 424/93.7; 435/2
(58) Field of Search ............................... 424/93.4, 93.7, 424/93.73; 435/2, 325

(56) References Cited

U.S. PATENT DOCUMENTS

| 4,971,794 A | 11/1990 | Linggood et al. ............. 424/92 |
| 5,017,372 A | 5/1991 | Hastings ..................... 424/85.8 |
| 5,891,860 A | 4/1999 | Heerze et al. ................. 514/53 |

FOREIGN PATENT DOCUMENTS

| SU | 1124976 A | * 11/1984 | .......... A61K/35/18 |

OTHER PUBLICATIONS

C. Ahren et al., (1993) "Intestinal antibody response after oral immunization with a prototype cholera B subunit–colonization factor antigen enterotoxigenic *Escherichia coli* vaccine" Vaccine, vol. 11, (9); 929–934.
F.J. Cassels et al., (1995) "Colonization factors of diarrheagenic *E. coli* and their intestinal receptors" J. Ind. Microbiol., vol. 15 (3): 214–226.
Dodge et al., (1963) "The Preparation and Chemical Characteristics of Hemoglobin–Free Ghosts of Human Erythrocytes" Arch. Biochem. Biophys., vol. 100, pp. 119–130.
M. Jertborn et al., (1998) "Safety and immunogenicity of an oral inactivated enterotoxigenic *Escherichia coli* vaccine" Vaccine, vol. 16 (2/3):255–260.
H. Ryu et al., (2001) "*Escherichia coli* Strain RDEC–1 AF/R1 Endogenous Fimbrial Glycoconjugate Receptor Molecules in Rabbit Small Intestine" Infect. Immun., vol. 69(2): 640–649.
M.K. Wolf et al., (1993) "Characterization of Enterotoxigenic *Escherichia coli* Isolated from U.S. Troops Deployed to the Middle East" J. Clin. Microbiol., vol. 31(4): 851–856.
F.K. De Graaf et al., "The Fimbrial Adhesins of *Escherichia coli*", pp. 65–143.
M. Jertborn et al., Vaccine, vol. 16, (1988), pp. 255–260.

Karl–Anders Karlsson, "Animal Glycosphingolipids as Membrane Attachment Sites for Bacteria", Annu. Rev. Biochem.. vol. 58, (1989), pp. 309–350.
Sami B. Khalil et al., "Characterization of an Enterotoxigenic *Escherichia Coli* Strain from Africa Expressing a Putative Colonization Factor", Infection and Immunity, vol. 67, No. 8, (1999), pp. 4019–4026.
Stuart Knutton et al., "Ultrastructural Study of Adhesion of Enterotoxigenic *Escherichia Coli* to Erythrocytes and Human Intestinal Epithelial Cells", Infection and Immunity, vol. 44, No. 2, (1984), pp. 519–527.
Myron M. Levine et al., "Lack of Person–To–Person Transmission of Enterotoxigenic *Escherichia Coli* Despite Close Contact", American Journal of Epidemiology, vol. 111, No. 3, pp. 347–355.
Myron M. Levine et al., "Immunity to Enterotoxigenic *Escherichia Coli*", Infection and Immunity, vol. 23, No. 3, (1979), pp. 729–736.
M. M. Levine et al., "Reactogencity, Immunogenicity and Efficacy Studies of *Escherichia Coli* Type 1 Somatic Pili Parenteral Vaccine in Man", Scand J. Infect. Dis. Suppl. vol. 33, (1982), pp. 83–95.
John L. Magnani et al., "A Monoclonal Antibody–Defined Antigen Associated with Gastrointestinal Cancer is a Ganglioside Containing Sialylated Lacto–N–Fucopentaose II", The Journal of Biological Chemistry, vol. 257, No. 23, (1982), pp. 14365–14369.
Heikki Peltola et al., "Prevention of Travellers' Diarrhoea by Oral B–Subunit/Whole–Celll Cholera Vaccine", The Lancet, vol. 338, (1991), pp. 1285–1289.
H. Ryu et al., Infect. Immun., vol. 69, (2001), pp. 640–649.
Barbara J. Stoll et al., "Local and Systemic Antibody Responses to Naturally Acquired Enterotoxigenic *Escherichia Coli* Diarrhea in an Endemic Area", The Journal of Infectious Diseases, vol. 153, No. 3, (1986), pp. 527–534.
Ann–Mari Svennerholm, "Serologic Differentiation Between Antitoxin Responses to Infection with Vibrio Cholerae and Enterotoxin–Producing *Escherichia Coli*", The Journal of Infectious Diseases, vol. 147, No. 3, (1983), pp. 514–522.
Carol O. Tacket et al., "Protection By Milk Immunoglobulin Concentrate Against Oral Challenge with Enterotoxigenic *Escherichia Coli*", The New England Journal of Medicine, vol. 318, No. 19, (1988), pp. 1240–1243.

(List continued on next page.)

*Primary Examiner*—David M. Naff
*Assistant Examiner*—Deborah K. Ware
(74) *Attorney, Agent, or Firm*—Elizabeth Arwine (57) ABSTRACT

Disclosed herein are RBC preparations and methods of making and using thereof for treating, preventing or inhibiting ETEC infections. In particular, bovine red blood cell (RBC) preparations are shown to reduce enterotoxigenic *Escherichia coli* (ETEC) adhesion when administered orally. Also disclosed are kits comprising RBC preparations for the treatment of ETEC infections.

13 Claims, 2 Drawing Sheets

OTHER PUBLICATIONS

M.K. Wolf et al., Clin. Microbiol., vol. 31, (1993), pp. 851–856.

C. Ahren et al., Vaccine, vol. 11, (1993), pp. 929–934.

Edwin H. Beachey, "Bacterial Adherence: Adhesin–Receptor Interactions Mediating the Attachment of Bacteria to Mucosal Surfaces", The Journal of Infectious Diseases, vol. 143, No. 3, (1981), pp. 325–345.

August L. Bourgeois et al., "Etiology of Acute Diarrhea Among United States Military Personnel Deployed to South America and West Africa", Am. J. Trop. Med. Hgy., vol. 48, No. 2, (1993), pp. 243–248.

F.J. Cassels et al., J. Ind. Microbiol., vol. 15, (1995), pp. 214–226.

Christopher P. Cheney et al., "Quantitation of the Adherence of an Enteropathogenic *Escherichia Coli* to Isolated Rabbit Intestinal Brush Borders", Infection and Immunity, vol. 26, No. 2, (1979), pp. 736–743.

Trinka S. Coster et al., "Safety, Immunogenicity, and Efficacy of Live Attenuated *Vibrio Cholerae* 0.139 Vaccine Prototype", The Lancet, vol. 345, (1995), pp. 949–952.

Dodge et al., Arch. Biochem. Biophys., vol. 201, (1962), pp. 119–130.

Charles D. Ericsson et al., "Travelers' Diarrhea: Approaches to Prevention and Treatment", Clinical Infectious Diseases, vol. 16, (1993), pp. 616–626.

Doyle J. Evans et al., "Hemagglutination Patterns of Enterotoxigenic and Enteropathogenic *Escherichia Coli* Determined with Human, Bovine, Chicken, and Guinea Pig Erythcrocytes in the Presence and Absence of Mannose", Infection and Immunity, vol. 23, No. 2, (1979), pp. 336–346.

Janina Goldhar, "[4] Erythrocytes as target Cells for Testing Bacterial Adhesins", Methods in Enzymology, vol. 253, pp. 43–50.

Enrique A. Gonzalez et al., "Comparative Study of Inhibition of Mannose–Resistant Haemagglutination Caused by CFA/I, CFA/II, K88 and K99–positive *Escherichia Coli* Strains", FEMS Microbiology Letters, vol. 29, (1985), pp. 115–121.

* cited by examiner

METHOD FOR TREATING, PREVENTING, OR INHIBITING ENTEROTOXIGENIC *ESCHERICHIA COLI* INFECTIONS WITH BOVINE RED BLOOD CELLS

ACKNOWLEDGMENT OF GOVERNMENT SUPPORT

This invention was made by employees of the United States Army. The government has rights in the invention.

BACKGROUND OF THE INVENTION

1. Field of the Invention.

This invention relates generally to bovine erythrocyte preparations. In particular, the present invention relates to methods of using bovine erythrocyte preparations for treating, preventing, or inhibiting enterotoxigenic *Escherichia coli* infections.

2. Description of the Related Art.

Diarrhea caused by enterotoxigenic *Escherichia coli* (ETEC), commonly referred to as travelers' diarrhea, is a common health problem among travelers visiting less developed or tropical countries. See Peltola, H., et al. (1991) Lancet 338:1285–1289 and Ericsson, C. D. et al. (1993) Clin. Infect. Dis. 16:616–626. Diarrhea caused by ETEC and other ETEC infections are important concerns for military personnel when deployed to less developed countries. See Wolf, M. K., et al. (1993) Clin. Microbiol. 31:851–856 and Bourgeois, A. L., et al. (1993) Am. J. Trop. Med. Hyg. 48:243–248. ETEC maybe transmitted by food or water contaminated with animal or human feces. ETEC produces two toxins, a heat-stable toxin (ST) and a heat-labile toxin (LT). ETEC infections may cause profuse watery diarrhea, abdominal cramping, fever, nausea, vomiting, chills, loss of appetite, headache, muscle aches, and bloating.

The current therapy for travelers' diarrhea is to initiate treatment with agents such as bismuth subsalicylate (Pepto-Bismol®), antidiarrheals such as diphenoxylate with atropine (Lomotil®), loperamide HCl (Immodium®), attapulgite (Kaopectate®) and the like, rehydration therapy, and combinations thereof. The majority of the treatments involve the non-specific removal of the offending agents (i.e. toxins) from the intestinal tract. Only in moderate to severe cases of diarrhea where distressing or incapacitating symptoms are reported is antimicrobial therapy recommended. ETEC is frequently resistant to common antibiotics such as trimethoprim-sulfamethoxazole and ampicillin. Fluoroquinolones such as ciprofloxacin have shown some efficacy. Antibiotics are not usually effective at reducing clinical symptoms of the disease and problems associated with antibiotic resistance can occur. Prophylactic use of antibiotics is not recommended. Thus, therapies that specifically remove ETEC from the intestine are needed to provide more effective treatments for ETEC diarrhea.

In order to initiate the infectious process of diarrhea, ETEC must adhere to the host intestinal epithelial cells via the binding between bacterial adhesins and host receptors. This binding is commonly referred to as adhesion-receptor interaction. See Beachey, E. H. (1981) J. Infect. Dis. 143:325–345; Satterwhite, T. K., et al. (1978) Lancet. 2:181–184; and Warner, L. and Y. S. Kim. (1989) "Intestinal Receptors for Microbial Attachment", Eds. M. J. G. Farthing, and G. T. Kensch, ENTERIC INFECTION: MECHANISMS, MANIFESTATIONS AND MANAGEMENT, pp. 31–40. Raven Press, N.Y. One treatment method that is based on this adhesin-receptor interaction, described by U.S. Pat. No. 5,897,860 ('860 patent), involves an oligosaccharide covalently attached to a solid support, wherein the oligosaccharide binds *E. coli* heat-labile toxin. The '860 patent does not prevent or treat ETEC infections as the methods merely immobilize or neutralize the heat-labile toxin (LT). Thus, the enterotoxigenic *E. coli* are still capable of adhering to the intestinal epithelial cells, colonizing and producing more LT.

Thus, a need still exists for a method for treating, preventing, or inhibiting ETEC infections, diseases, or disorders such as travelers' diarrhea.

SUMMARY OF THE INVENTION

The present invention generally relates to erythrocyte (RBC) preparations, such as bovine erythrocyte (bRBC) preparations and methods using thereof for treating, preventing, or inhibiting enterotoxigenic *E. coli* (ETEC) infections.

In some embodiments, the present invention relates to a formulation for treating, preventing, or inhibiting an enterotoxigenic *E. coli* (ETEC) infection, such as travelers' diarrhea or infant diarrhea, comprising a therapeutically effective amount of at least one RBC preparation and a carrier suitable for oral administration. The formulation may further comprise at least one supplementary active compound such as an anti-diarrheal or an antibiotic. Preferred supplementary active compounds include bismuth subsalicylate, diphenoxylate with atropine, loperamide HCl, attapulgite, and ciprofloxacin. The formulation may further include a composition that binds LT. In some preferred embodiments, the formulation comprises a carrier such as an ingestible carrier. The carrier may be a pharmaceutical carrier or a foodstuff.

In some preferred embodiments, the RBC preparation is a bovine RBC preparation. The RBC preparation may comprise whole erythrocytes, erythrocyte ghosts, erythrocyte fractions, erythrocyte extracts, glycolipid receptors isolated from erythrocytes, or combinations thereof.

In some embodiments, the present invention relates to a method of treating, preventing, or inhibiting an ETEC infection in a subject comprising administering to the subject a formulation comprising a therapeutically effective amount of at least one RBC preparation and a carrier suitable for oral administration. The method may further comprise administering to the subject at least one supplementary active compound such as a supplementary active compound is an anti-diarrheal or an antibiotic. Preferred supplementary active compounds include bismuth subsalicylate, diphenoxylate with atropine, loperamide HCl, attapulgite, and ciprofloxacin. In some embodiments, the method may further comprise administering to the subject a composition that binds LT.

In some embodiments, the present invention relates to a method of preventing, inhibiting, or reducing an amount of enterotoxigenic *E. coli* (ETEC) adhering to a subject's intestinal wall comprising administering to the subject a formulation comprising a therapeutically effective amount of at least one RBC preparation and a carrier suitable for oral administration. In some embodiments, the amount of ETEC adhering to the subject's intestinal wall is prevented, inhibited, or reduced by about 10% or greater, preferably about 20% or greater, more preferably, about 30% or greater, more preferably, about 40% or greater, most preferably, about 50% or greater.

In some embodiments, the present invention relates to a kit for the treatment, prevention, or inhibition of an enterotoxigenic *Escherichia coli* (ETEC) infection comprising a formulation comprising a therapeutically effective amount of at least one RBC preparation and a carrier suitable for oral administration packaged together with directions for use. The kit may comprise the formulation in individual doses. In some embodiments, the kit may comprise a food, a foodstuff, or a food supplement. The kit may further comprise a supplementary active compound.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

This invention is further understood by reference to the drawings wherein.

DETAILED DESCRIPTION OF THE INVENTION

The present invention generally relates to erythrocyte (RBC) preparations and methods using thereof for treating, preventing, or inhibiting enterotoxigenic *E. coli* (ETEC) infections. As used herein "RBC preparations" include whole erythrocytes, erythrocyte ghosts, erythrocyte fractions, erythrocyte extracts, glycolipid receptors isolated from RBCs, and combinations thereof. As used herein "erythrocyte fractions" means any part of the erythrocyte rather than the intact whole erythrocyte and includes soluble extracts, debris, ghosts, and the like. As used herein "ETEC infections" include infections caused by ETEC such as travelers' diarrhea, infant diarrhea, and the like. In preferred embodiments, the RBC preparations are bovine RBC (bRBC) preparations which include whole bovine erythrocytes, bovine erythrocyte ghosts, bovine erythrocyte fractions, bovine erythrocyte extracts, glycolipid receptors isolated from bovine RBCs, and combinations thereof.

As disclosed herein, adhesion of ETEC to host epithelial cells may be prevented, inhibited, or reduced by binding to RBC preparations such as bRBC preparations. Specifically, prevention, inhibition, or reduction of ETEC adhesion may be achieved by competitive binding to bRBC preparations as the binding affinity between ETEC and bovine erythrocytes is greater than the binding affinity between ETEC and intestinal epithelial cells. Consequently, ETEC infections may be treated, prevented, or inhibited by outcompeting the adhesion of ETEC to intestinal epithelial cells with the greater binding affinity of ETEC to bRBC preparations, by adsorbing off adherent ETEC from the host epithelial cell receptors with bRBC preparations, or a combination thereof. Thus, the present invention provides a method of treating, preventing, or inhibiting an ETEC infection in a subject comprising administering to the subject at least one bRBC preparation.

Examples of ETEC strains that are known to adhere to and agglutinate bovine erythrocytes (comprising receptors) include strains expressing colonization factors (CF, the adhesion protein) such as CFA/I, CFA/III, CS1, CS2, CS4, CS5, CS7, CS15, CS17, CS19, PCF0159 and PCF0166. See Cassels, F. J., and M. W. Wolf (1995) J. Ind. Microbiol. 15:214–226; De Graaf, F. K., and F. R. Mooi (1986) Adv. Microb. Physiol. 28:65–143; Evans, D., Jr., et al. (1979) Infect. Immun. 23:336–346; Khalil, S. B., et al. (1999) Infect. Immun. 67:4019–4026; and Ryu, H., et al. (2001) Infect. Immun. 69:640–649, which are herein incorporated by reference.

The ability of the RBC preparations of the present invention to prevent, inhibit, or reduce adhesion of ETEC to the intestinal wall of a subject may be measured by any of the methods available to those skilled in the art, including in vitro and in vivo assays. See e.g. Evans, D., et al. (1979) Infect. Immun. 23:336–346; Foldhar, J. (1995) Methods Enzymology 253:43–50; Gonzolez, E. A., et al. (1985) FEMS Microbiol. Lett. 29:115–121; and Knutton, S., et al. (1984) Infect. Immun. 44:519–527, which are herein incorporated by reference. Examples of suitable assays for activity measurements are provided herein. Properties of the preparations may be assessed, for example, by using one or more of the assays set out in the Examples below or those known in the art. Other pharmacological methods conventional in the art may be used to determine the efficacy of the RBC preparations for treating, preventing, or inhibiting ETEC infections.

The RBC preparations in accordance with the present invention are useful in the treatment of ETEC infections, preferably travelers' diarrhea, infant diarrhea, and the like. The RBC preparations of the present invention may be used in combination with or as a substitution for treatments of ETEC infections and related conditions. For example, the RBC preparations may also be used alone or in combination with at least one supplementary active compound such as bismuth subsalicylate, diphenoxylate with atropine, loperamide HCl, attapulgite, ciprofloxacin, and the like to treat, prevent or inhibit ETEC infections. Additionally, the RBC preparations may be used alone or in combination with compositions which bind *E. coli* heat-labile toxin (LT) such as those described in U.S. Pat. No. 5,891,860, which is herein incorporated by reference.

A RBC preparation of the present invention may be administered in a therapeutically effective amount to a mammal such as a human. Therapeutically effective amounts of the RBC preparations may be used to treat, prevent, or inhibit ETEC infections. An "effective amount" is intended to mean that amount of a RBC preparation that, when administered to a subject, is sufficient to prevent, inhibit, or reduce adhesion of ETEC to the intestinal wall of the subject or reduce the severity of symptoms, e.g. from severe to moderate. A "therapeutically effective amount" of a given RBC preparation, is a quantity sufficient to treat, prevent, or inhibit ETEC infections in a subject. The amount of a given RBC preparation that will correspond to such an amount will vary depending upon factors such as the particular RBC preparation, the formulation and route of administration, the ETEC strain, and the identity of the subject being treated, but can nevertheless be routinely determined by one skilled in the art. Also, as used herein, a "therapeutically effective amount" of a given RBC preparation of the present invention is an amount that prevents, inhibits, or reduces the amount of ETEC adhering to the intestinal wall of a subject as compared to a control by routine methods known in the art.

For example, a therapeutically effective amount of a RBC preparation of the invention ranges from about 0.001 to about 1,000 mg total dry weight per kg body weight, preferably about 0.001 to about 500 mg total dry weight per kg body weight, and more preferably about 0.001 to about 250 mg total dry weight per kg body weight. The skilled artisan will appreciate that certain factors may influence the amount of the RBC preparation required to effectively treat a subject, including but not limited to the severity of the ETEC infection, previous treatments, the general health and/or age of the subject, and other diseases present.

Moreover, treatment of a subject with a therapeutically effective amount of the RBC preparation preferably includes a single treatment, but can include a series of treatments. For example, a subject may be treated with a RBC preparation of the invention at least once. However, the subject may treated with the RBC preparation from about one time per week to about once daily for a given treatment period. The length of the treatment period will depend on a variety of factors such as the severity of the ETEC infection, the period of exposure to ETEC, the risk of ETEC infection, and the like. It will also be appreciated that the effective dosage of the RBC preparation used for treatment may increase or decrease over the course of a particular treatment. Changes in dosage may result and become apparent by standard diagnostic assays known in the art. In some instances chronic administration may be required. The RBC preparation may be administered before ETEC exposure or infection, during ETEC exposure or infection, after ETEC exposure or infection, or a combination thereof.

The RBC preparations of the invention can be incorporated into formulations suitable for the intended route of administration. Preferred routes of administration include oral administration. Formulations suitable for oral administration are well known in the art. The formulations of the present invention comprise a therapeutically effective amount of at least one RBC preparation and an inert, carrier or diluent. As used herein, the carrier or diluent may be an ingestible carrier or a pharmaceutically acceptable carrier. Suitable ingestible carriers include food, foodstuffs, and food supplements, such as red meat, milk, protein drinks, and nutritional sports bars. Pharmaceutically acceptable carriers include solvents, dispersion media, coatings, antibacterial and antifungal agents, isotonic and absorption delaying agents, and the like that are compatible with oral administration. The carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate, and the like. Except insofar as any conventional media or agent is incompatible with RBC formulations, use thereof in the formulations is contemplated.

Supplementary active compounds can also be incorporated into the formulations. Supplementary active compounds include bismuth subsalicylate, diphenoxylate with atropine, loperamide HCl, attapulgite, ciprofloxacin, and the like commonly used to treat ETEC infections. Additionally, compositions that bind LT such as those described in U.S. Pat. No. 5,891,860, may be incorporated into the formulations.

In preferred embodiments, the RBC preparation of the present invention is formulated to be compatible with oral administration. A variety of formulations can be employed. Thus, if a solid carrier is used, the formulation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, or suspension in an ampoule or vial.

The formulations of the invention may be manufactured in manners generally known for preparing pharmaceutical formulations and food supplements, e.g., using conventional techniques such as mixing, dissolving, granulating, drageemaking, levigating, emulsifying, encapsulating, entrapping or lyophilizing. For oral administration, the RBC preparations can be formulated readily by combining the RBC preparations with carriers known in the art such as those used in pharmaceuticals or nutritional supplements. Such carriers enable the RBC preparations of the invention to be formulated as tablets, pills, dragees, capsules, liquids, gels, syrups, slurries, suspensions and the like, for oral ingestion by a subject to be treated. Formulations for oral use can be obtained using a solid excipient in admixture with at least one RBC preparation, optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally comprise gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds and agents.

Oral formulations of the present invention include push-fit capsules made of gelatin, as well as soft, sealed capsules made of gelatin and a plasticizer, such as glycerol or sorbitol. The push-fit capsules can comprise the RBC preparation of the present invention in admixture with fillers such as lactose, binders such as starches, and/or lubricants such as talc or magnesium stearate, and, optionally, stabilizers. In soft capsules, the RBC preparation may be dissolved or suspended in suitable liquids, such as fatty oils, liquid paraffin, or liquid polyethylene glycols. In addition, stabilizers may be added. All formulations for oral administration should be in dosages suitable for such administration. Thus, the RBC preparations of the invention are preferably prepared in a unit-dosage form appropriate for oral administration.

Oral formulations generally include an inert diluent or an edible carrier. They can be enclosed in gelatin capsules or compressed into tablets. For the purpose of oral therapeutic administration, the RBC preparation can be incorporated with excipients and used in the form of a tablet, a bolus, a troche, or a capsule which may comprise any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Some preferred formulations for oral formulations include microcrystalline tablets, gelatin capsules, or the like.

Additionally, the compounds may be delivered using a sustained-release system, such as semi-permeable matrices of solid hydrophobic polymers comprising the RBC preparation. Various sustained-release materials have been established and are known by those skilled in the art. Sustained-release capsules may, depending on their chemical nature, release the RBC preparation for a few weeks up to over 100 days. Depending on the chemical nature and the biological stability of the RBC preparation, additional strategies for protein stabilization may be employed. The formulations also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

In some embodiments, the RBC preparations are prepared with carriers that will protect the RBC preparations against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit comprising a predetermined quantity of a RBC preparation calculated to produce the desired therapeutic effect in association with the required carrier. The specification for the dosage unit forms of the invention are dictated by and directly dependent on the unique characteristics of the RBC preparation and the particular therapeutic effect to be achieved, and the limitations inherent in the art of compounding such a RBC preparation for the treatment of individuals. Preferred formulations include bRBC preparations in an enteric coated capsule that releases the bRBC preparation into the small intestine of a subject where the interactions with ETEC would occur.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The following examples are intended to illustrate but not to limit the invention.

EXAMPLE 1

RBC Ghost Preparation

RBC preparations were made according to a modified procedure described by Dodge et al. (1962) Arch. Biochem. Biophys. 201:119–130, which is herein incorporated by reference. Specifically, 15 ml of blood in acid-citrate-dextrose solution (ACD) (Sigma Chemical, Co., St. Louis, Mo.) was placed in a 50 ml plastic (or glass) tube and centrifuge at 1,300 g (Sorvall RC-3 with HL-8 rotor, at 2000 rpm) for 15 minutes. The Buffy coat (a white layer primarily comprising lymphocytes formed between plasma (top) and packed RBC (bottom) when blood in an anticoagulant such as ACD) was first centrifuged, and then the supernatant fluid containing serum was aspirated off.

Then the RBC pellet was washed up to four times by filling the tube with normal saline (0.9% NaCl in $H_2O$, 9 g/L), resuspending the RBC by gently rocking the tube for several times and centrifugation as before. The RBC pellet was washed until the supernatant was clear, but no more than 4 times. Then the RBC pellet was resuspended in isotonic PBS, 50 mM, pH. 7.4 (1 volume of sodium phosphate monobasic solution ($NaH_2PO_4$, 0.155 M, 18.6 g/L) to 6 volumes of sodium phosphate dibasic solution ($Na_2HPO_4$-$7H_2O$, 0.103 M, 27.6 g/L)), and incubated in an ice bath for 30 minutes. After the ice bath incubation, the RBC solution was centrifuged as before and the supernatant was aspirated off.

Three (3) ml of the packed RBC was transferred to a 40 ml Nalgene tube (Nalge Nunc International, Rochester, N.Y.) containing 30 ml of a hypotonic buffer solution (1:16 dilution of isotonic PBS in $H_2O$), pH. 7.4, and then mixed on a Thermolyne Varimix (Barnstead/Thermolyne, Dubuque, Iowa) for 15 minutes at room temperature followed by centrifugation at 25,000 g (Sorvall RC-5B with SS-34 rotor, at 14,400 rpm) for 15 minutes. The supernatant was aspirated off and the pellet (RBC ghost) was resuspended, washed in the hypotonic buffer solution, and centrifuged three times. Then the supernatant was aspirated off and the pellet was stored in $-70°$ C. until further use.

It is noted that 4 of 10 liters of blood obtained from a cow yielded 540 ml of packed RBC ghosts (about 3.8 g total protein). Thus, large scale production could comprise obtaining about 500 ml of blood per week per each cow in a herd of about 200 cattle (or about 2–5 sacrifices) per year would provide economically feasible amounts of RBC preparations.

EXAMPLE 2

Agglutination Assays

Tables 1–4 below show the agglutinating properties of bRBC preparations with human ETEC strains. For each, ETEC strains were grown on colonization factor antigen (CFA) agar (Becton Dickinson, Sparks, Md.) or CFA agar comprising 0.15% bile salts (Becton Dickinson, Sparks, Md.) at 37° C. overnight and the bacteria were harvested in phosphate buffered saline (PBS, pH 7.4). The bacterial concentration was adjusted to 10× of 0.5 optical density at 600 nm for standardization, 2% bRBC was prepared in phosphate buffered saline (PBS) comprising 50 mM α-methyl mannopyranoside (Sigma Chemical, Co., St. Lois, Mo.). For the slide hemagglutination assays, 8 μl of the ETEC suspension was mixed with the same volume of 2% RBC on a microscopic slide for 2 minutes. The degree of hemagglutination was observed visually and graded based on the clump size and time of agglutination (see score of agglutination, Table 3).

Table 1 shows the ability of bRBC to agglutinate human ETEC strains.

TABLE 1

Hemagglutinating activity of various ETEC strains with bovine erythrocytes

| ETEC Strain | Colonization Factor | Hemagglutination |
|---|---|---|
| H10407 | CFA/I+ | + |
| H10407P | CFA/I− | − |
| H10407NM | CFA/I+ | + |
| M452C1 | CFA/I+ | + |
| Z26-5 | CFA/III+ | + |
| 60R75 | CS 1+ | + |
| M424C1 | CS 1+, CS 3+ | + |
| C91f | CS 2+ | + |
| E9034A | CS 3+ | ± |
| E8775 | CS 4+, CS 6+ | Autoagglutination |
| E11881B | CS 4−, CS 6− | − |
| E11881E | CS 4+, CS 6+ | − |
| E17018A | CS 5+, CS 6+ | + |
| E17018B | CS 5−, CS 6− | − |
| PE423 | CS 5 | − |
| D02-2 | CS 7+ | + |
| E20738A | CS 17+ | + |
| E20738B | CS 17− | − |
| C95-1059 | CS 19 | + |
| Z78-6 | PCF 0159+ | + |
| G723 | PCF 0159− | − |
| Z163-3 | PCF 0166+ | + |

Table 2 shows the ability of bRBC and its ghost preparation to agglutinate several ETEC strains.

TABLE 2

Agglutination of a bRBC and fractions by several ETEC strains

| | ETEC Strain | | | | |
|---|---|---|---|---|---|
| Fraction | E11881E | M424C1 | 60R75 | H10407NM | H10407P |
| | CS4, CS6 | CS1, CS3 | CS1 | CFA/I | CFA/I negative |
| Hemagglutination with RBC | − | + | + | + | − |
| RBC ghosts | − | + | + | + | − |

Table 3 shows differences in hemagglutination with human ETEC strains between RBCs from two individual cows.

TABLE 3

Differences in hemagglutination with human ETEC strains between erythrocytes from two individual cows

| ETEC strain | Cow number* | |
|---|---|---|
| (Colonization Factor) | No. 8884 | No. 9654 |
| H10407 NM (CFA/I) | 3** | 0 |
| 60R75 (CS1) | 4 | 3 |
| C91f (CS2) | 3 | 0 |
| M424C1 (CS1, CS3) | 4 | 3 |
| E17018A (CS5, CS6) | 3 | 2 |
| E20738A (CS17) | 4 | 4 |
| Z163-3 (PCF0166) | 3 | 0 |

*USDA Bovine Mastitis Laboratory Designation (Beltsville, MD).
**Score of agglutination: 4, agglutination <10 sec; 3, agglutination 10–30 sec; 2, agglutination 0.5–1 min; 1, agglutination 1–2 min; 0, no agglutination within 2 min.

Table 4 compares the agglutinating ability of intact RBC and its ghost preparation with human ETEC strains.

TABLE 4

Agglutination of intact bovine erythrocyte (Cow No. 8884) and its ghost preparation with human ETEC strains

| | ETEC strain | |
|---|---|---|
| (Colonization Factor) | Whole bRBC | bRBC ghost |
| H10407 NM (CFA/I) | 3* | 3 |
| 60R75 (CS1) | 4 | 3 |
| C91f (CS2) | 3 | 3 |
| M424C1 (CS1, CS3) | 4 | 3 |
| E17018A (CS5, C56) | 3 | 3 |
| E20738A (CS17) | 4 | 4 |
| Z163-3 (PCF0166) | 3 | 2 |

*Score of agglutination: 4, agglutination <10 sec; 3, agglutination 10–30 sec; 2, agglutination 0.5–1 min; 1, agglutination 1–2 min; 0, no agglutination within 2 min.

EXAMPLE 3

RBC Preparation Stability

The stability of the RBC ghost preparations was tested by the slide agglutination assay described in Example 2. The RBC ghost preparations were stored at −20° C. and −70° C. About every two to four months, the preparations were thawed and used for the agglutination assay. The remaining preparations were frozen and stored again at −20° C. and −70° C.

The repeated freezing and thawing up to 5 times did not alter the original agglutination activity of the ghost preparation. Thus, storage of the RBC ghost preparation at −20° C. and −70° C. did not alter the original agglutination activity as compared to the intact bRBC preparations.

EXAMPLE 4

Analysis of Glycolipid Receptors Isolated from bRBC Ghosts

Figure 3:
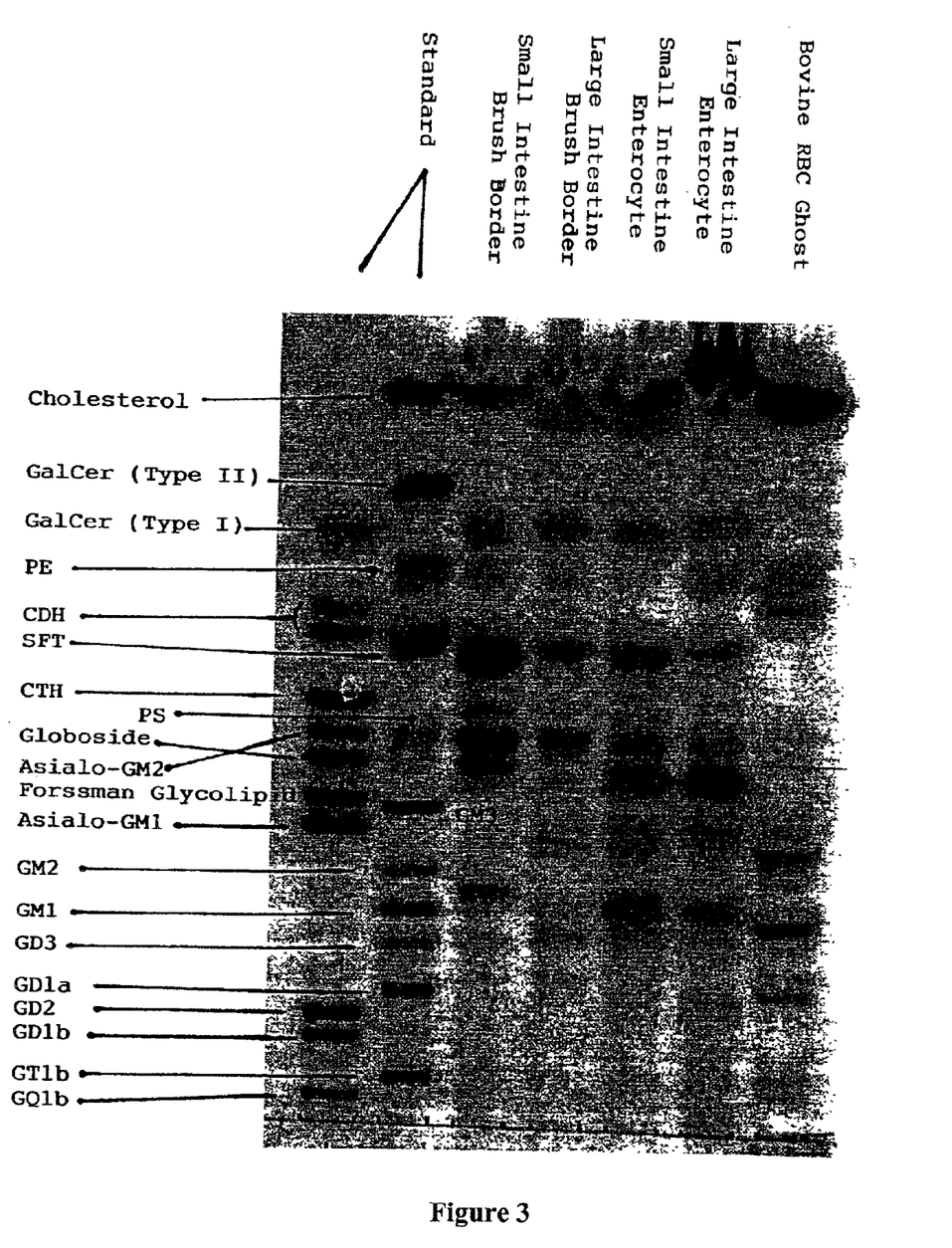
FIG. 3. Lipid profiles of bRBC and rabbit intestinal tissue extracts by high performance thin layer chromatography.

Glycolipids and phospholipids were extracted from the bRBC ghosts by methanol:chloroform:water (10:5:3) extraction. The lipid profile of the RBC ghost was analyzed by high performance thin layer chromatography (HPTLC) and adherence of human ETEC strains to the lipid extraction of RBC ghost was examined by HPTLC overlay procedure with $^{14}$C-labeled ETEC strain. See Magnani, J. et al. (1982) JBC 257:14365, which is herein incorporated by reference. As show in the HPTLC orcinol plate, the RBC ghost was found to contain several glycolipids and phospholipids, such as asialo-GM2, asialo-GM1, GM1, lactosylceramide and phosphyatidylethanolamine, that are well-known receptors for many human ETEC strains. See FIG. 3, see also Karlsson, K. A. (1989) Ann. Rev. Biochem. 58:309–350, which is herein incorporated by reference. Also several ETEC strains (E9034A, 60R315, C91f, and the like) were found to bind the lipid extract of bRBC by the HPTLC overlay procedure.

EXAMPLE 5

Absorptive Capacity and Competition Assay

To examine the absorptive capacity of bRBC, 2% intact bRBC (diluted to 0.1% and 0.01% total volume) was mixed with an optically adjusted ETEC H10407 ($2.2 \times 10^9$ bacteria/ml) suspension and incubated at 37° C. for two minutes (Table 5). At 2, 5, 10, 20, and 60 minutes after incubation, 0.1 ml was taken out of the bactera-bRBC mixture followed by centrifugation at 1,300 g for 2 minutes at room temperature to remove the adherent bacteria to bRBC. The supernatant fluid (free suspended bacteria) was serially diluted 1:10 and inoculated on CFA agar plates in duplicates followed by overnight incubation at 37° C. See e.g. Cheney, C. P., et al. (1979) Infect. Immun. 26:736–743, see also Wenneras, C., et al. MOLECULAR PATHOGENESIS OF GASTROINTESTINAL INFECTIONS. Plenum Press, N.Y. (1991), pp. 327–330, both of which are herein incorporated by reference. Table 5 shows the ability of erythrocytes to remove ETEC strains in vitro. Specifically, it was found that mixing intact RBC, 0.1% and 0.01% total volume, with a CFA/I bearing H10407 suspension that the bacterial concentration was reduced by 59% and 57% after 2 minutes incubation, respectively since the numbers of the free suspended bacteria at 0.1% and 0.01% bRBC after removal of the adherent bacteria to bRBC were 41% and 43% of the control (unabsorbed with bRBC), respectively.

TABLE 5

Reduction of *E. coli* H10407 (CFA/I) colony counts by bRBC

| | Number of bacteria* | |
|---|---|---|
| Incubation Time (minutes) | 0.1% RBC | 0.01% RBC |
| 2 | $9.1 \times 10^7$ (41%) | $9.5 \times 10^7$ (43%) |
| 5 | $1.1 \times 10^8$ (49%) | $1.7 \times 10^8$ (76%) |
| 10 | $1.1 \times 10^8$ (50%) | $1.7 \times 10^8$ (76%) |
| 20 | $9.8 \times 10^7$ (45%) | $1.3 \times 10^8$ (60%) |
| 60 | $3.5 \times 10^8$ (159%) | $5.6 \times 10^8$ (255%) |

*Control: $2.2 \times 10^8$ bacteria/ml.

Figure 1:
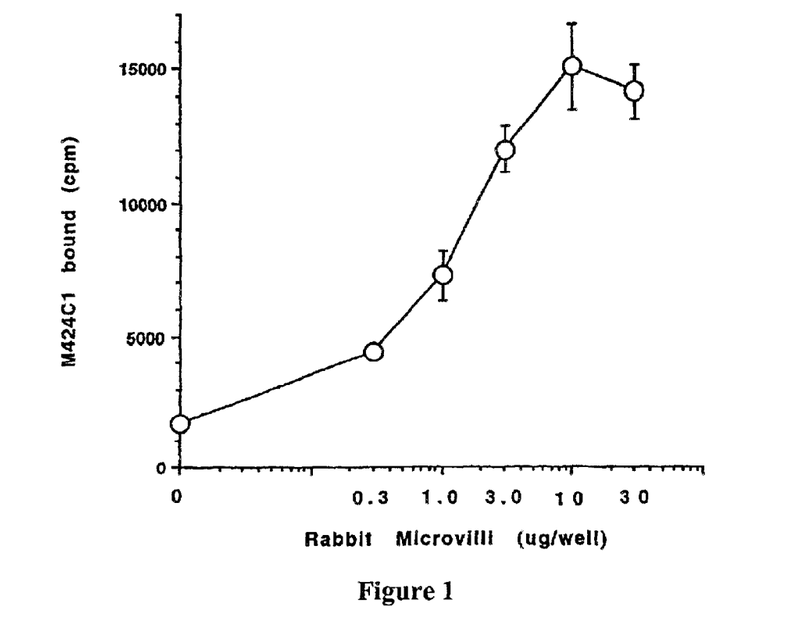
FIG. 1. Adherence of a human ETEC M424C1 (CS1, CS3) to rabbit small intestinal microvilli (n=3).
Figure 2:
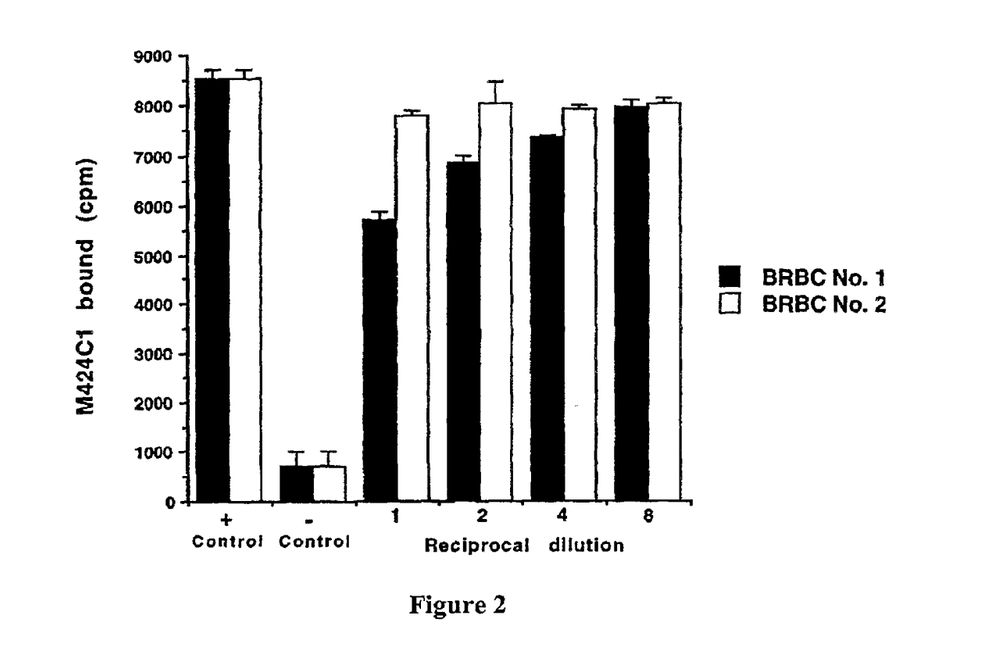
FIG. 2. Removal of a human enterotoxigenic *Escherichia coli* strain M424C1 (CS1, CS3) attached to rabbit small intestinal microvilli by bovine erythrocytes (n=2). Agglutination scores: BRBC No. 1, 4+; BRBC No. 2.1+.

For the competition assay, rabbit brush borders (RBB) were prepared according to Ryu, H et al.(2001) Infect. Immun. 69:640–649, which is herein incorporated by reference. A bacterial adherence assay was conducted by mixing 50 μl of RBB (1 mg/ml protein), 30 μl of PBS and 20 μl of an ETEC strain, M424C1 (CS 1,3), which binds to RBB in a glass test tube in duplicates. After incubation for 15 minutes at room temperature on a rotating platform, the tubes were mixed vigorously for 10 seconds on setting 5 with Vortex-Geni (Scientific Industries, Bohemia, MY). The bacteria-RBB mixture was washed twice with PBS by centrifugation, at 1,100 g for 10 minutes and the pellet was gently resuspended in 100 μl of PBS. Ten (10) μl of 2% bRBC and PBS were added to the competition assay tube and control tube, respectively, followed by incubation for 5 minutes at room temperature on a rotating platform. The bacterial adherence to RBB was examined at 1,000 power in oil immersion utilizing Nomarski differential interface phase contrast optics (Olympus USAH2). FIGS. 1 and 2 show the ability of bovine erythrocyte ghosts to remove the adherent bacteria from the RBB microvilli. When examined under a phase contrast microscope, the RBC ghosts attached to ETEC that were bound to the brush borders, and appeared to be competing off RBB-bound bacteria away from the RBB.

EXAMPLE 6

In vivo Assay in Human Subjects

To determine whether a given RBC preparation is effective in preventing, inhibiting, or treating a disease or infection associated with enterotoxigenic *E. coli*, the following assay may be conducted. To determine whether the given RBC preparation is effective to prevent or treat an ETEC disease or infection, the RBC preparation is administered to subjects before or during the challenge with the ETEC strain. To determine whether the given RBC preparation is effective to treat an ETEC disease or infection, the RBC preparation is administered after the onset of symptoms of ETEC infection after challenge with the ETEC strain.

An ETEC strain, such as H10407, may be used. See Levine, M. M., et al. (1982) Scand. J. Infect. Dis. 33:83–95; Levine, M. M., et al. (1979) Infect. Immun. 23:729–736; Levine, M. M., et al. (1980) Am. J. Epidemiol. 111:347–355; and Tacket, C. O., et al. (1988) N. Engl. J. Med. 318:1240–1243, which are herein incorporated by reference. To a liquid culture of the ETEC strain, glycerol is added and then the culture is frozen in small aliquots at $-70°$ C.$\pm 10°$ C. Master and production seed stocks of the ETEC strain are prepared under current good manufacturing practices (GMP). At about 18 to about 22 hours before the ETEC challenge, the required orally inocula are obtained by thawing a single frozen vial and inoculating multiple agar plates for overnight culture. The bacteria are harvested, suspended in sterile saline and read at 600 nm in a spectrophotometer. The concentration of cells is adjusted to a stock solution of about $10^{10}$ to about $10^9$ cfu/ml. The bacterial suspension may be diluted in saline. One (1) ml of the bacterial suspension is administered to each subject.

The number of viable cfu (colony-forming units) administered to a human subject may be determined retrospectively by serially diluting, plating, and averaging the inoculum given to each subject (pre- and post-challenge). Each dilution is done in triplicate. One (1) ml of a bacterial suspension containing the target number of cfu is mixed with 30 ml of sodium bicarbonate, 2 g of $NaHCO_3$ per 150 ml of sterile, deionized water. This mixture is ingested by the subject about 2 minutes after ingestion of 120 ml of the sodium bicarbonate solution. At least 90 minutes before and after the challenge, each subject should fast.

Subjects used for this assay should have a medical examination and be determined to be in good health. Subjects should have regular bowel habits, at least three stools (of normal consistency) per week and two or fewer stools per day, without frequent use of laxatives or antidiarrheal agents. Persons who were previously exposed or possibly exposed to ETEC or cholera bacteria, are allergic to quinolones, or have any significant gastrointestinal abnormality should be excluded as well as pregnant females, those being human immunodeficiency virus, hepatitis B surface antigen or hepatitis C virus positive, those being treated with antibiotics, theophylline, iron, zinc, histamine, H-2 receptor antagonist or proton pump inhibitors, or those having febrile illness within 48 hours prior to admission.

A double blind study may be conducted over a given period of time, such as two weeks. Following ETEC challenge, each subject is assessed about 3 to about 4 times daily for reactions to the challenge. Symptoms are graded as mild (no limitation in activity, no intervention needed), moderate (mild-to moderate limitation in activity; no or minimal treatment and/or intervention needed), or severe (unable or difficult to perform daily activities and treatment and/or intervention needed). Vital signs are recorded at least three times a day and fever is defined as an oral temperature of greater than about 100.5° F. Each stool output is collected, weighed, assessed for presence of blood and graded as previously described. See Coster, T. S., et al. (1995) Lancet 345:949–952, which is herein incorporated by reference.

Any diarrhea is further classified as mild, moderate, and severe. Mild diarrhea is defined as two to three loose stools, which did not exceed 400 g diarrheal stools pre 24 hours. Moderate diarrhea is four to five loose stools with 401 to 799 g diarrheal stools per 24 hours. Severe diarrhea is defined as six or more loose stools with 800 g or higher weight of diarrheal stool per 24 hours, or two loose stools/day, regardless of stool weight, and fever. Severe diarrhea must also meet at least two of the following symptoms graded as severe, including headache, nausea, generalized aches, abdominal cramps, gas, emesis, malaise, or fatigue. Colonization is defined as a positive test for the ETEC challenge strain in two stool cultures collected at least 24 hours post-challenge.

Stool samples from each subject are weighed and streaked directly onto MacConkey agar culture medium. Spread plates are inoculated after taking about 0.1±0.01 g of stool and making 100 fold serial dilutions in phosphate buffer solution. Each dilution are plated onto MacConkey agar. Stool samples (or rectal swabs if no stool sample is produced) collected between the 0700 and 1900 hours are plated immediately. Samples collected at other times are suspended in buffered glycerol saline, refrigerated at 4° C., and streaked for colony isolation the following day. Presumptive ETEC isolates are confirmed by colony blot, with detection by antisera raised in New Zealand white rabbits specific for the given strain antibody. Stool is considered negative for ETEC if no *E. coli* are isolated or are negative by immunoblot in about ten picked colonies.

After the collected stool is weighed, small amounts of stool specimens are immediately stored at −70° C. Fecal antibodies are extracted by the Ahren's procedure. See Ahren, C., et al. (1993) Vaccine 11:929–934. Five grams of thawed stool is mixed with 5.0 ml of solution containing STI (100 mg/ml) (Sigma, St. Louis, Mo.), EDTA (0.05M), and PMSF (10 mM) (Sigma), dissolved in PBS supplemented with 0.05% Tween 20 (Sigma). The mixture is left to stand at the room temperature for 15 minutes with intermittent shaking and then centrifuged at 20,000×g for 30 minutes. Bovine serum albumin (final concentration, 0.1%: weight/volume) (Sigma) and sodium azide (final concentration, 0.02%) (Sigma) are added to the supernatant after the pellet is discarded. Aliquots of the fecal extract supernatant are stored at −70° C. until assayed for total and specific IgA antibody contents by ELISA. See Jertborn, M., et al. (1988) Vaccine 16:255–260, Stoll, B. J., et al. (1986) J. Infect. Dis. 153:527–534; and Svennerholm, A. M., et al. (1983) J. Infect. Dis. 147:514–522, which are herein incorporated by reference.

The total IgA content in the fecal extract samples may be determined by a modified ELISA method by using a human colostral IgA reference (Sigma) as a standard. Specimens with an IgA concentration of less than about 10 $\mu$g/ml should be excluded from further analysis, since antibody titrations of specimens with IgA concentration of less than about 10 $\mu$g/ml give unreliable results. Specific antibody levels in the fecal extracts are determined using conventional ELISA methods known in the art. To adjust for variations in the IgA content in the stool samples collected from different persons and on different days, fecal extract antibody titers are expressed as units per microgram and re obtained by dividing the specific titer (in units per milliliter) by the total IgA content (in micrograms per milliliter), and multiplying by 10. About a 2-fold or greater increase in the titer of specific IgA per total IgA content between pre- and post-challenge specimens is considered to be a responder.

Exploratory data analyses of the ETEC strains and doses with all measured parameters are performed at periods, including the control baseline prior to ETEC challenge, post-challenge of ETEC to initiation of antibiotic treatment, and initiation of antibiotic treatment plus 48 hours. See SAS/STAT User's Guide, Version 6, 2:1007–1069, SAS Inst. Inc., Cary, N.C. 27513. Some data are analyzed by Fisher exact 2-tailed test at a 95% confidence level. A Student t-test may also be applied in certain cases. Furthermore, clinical symptoms expressed in the occurrence ratios (reported cases/all infected volunteers) are compared between different and the same sexes. SPSS Base 10 software (SPSS Inc., Chicago, Ill.) was used to analyze the immunological data, while other data were analyzed by the SAS programs.

Generally, control subjects (not administered a given RBC preparation) should exhibit a mean onset time of diarrhea and colonization at about 8 to about 60 hours. After oral challenge with the given ETEC strain, the first detection of fecal ETEC and shedding post-challenge in the control subjects should be about 3 to about 60 hours. Symptoms of ETEC infection include diarrhea, headache, gurgling, abdominal cramps, nausea, vomiting, appetite loss, fatigue, tenesmus, fever, emesis, malaise and lightheadedness.

An effective RBC preparation will prevent, inhibit, or reduce the symptoms associated a disease or infection caused by the ETEC challenge strain.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method of treating, preventing, or inhibiting an enterotoxigenic *Escherichia coli* (ETEC) infection in a subject comprising orally administering to the subject a therapeutically effective amount of a preparation containing isolated bovine red blood cells (RBC) and a carrier suitable for oral administration.

2. The method of claim 1, further comprising administering to the subject at least one supplementary active compound.

3. The method of claim 1, wherein the supplementary active compound is an anti-diarrheal or an antibiotic.

4. The method of claim 1, wherein the supplementary active compound is bismuth subsalicylate, diphenoxylate with atropine, loperamide HCl, attapulgite, or ciprofloxacin.

5. The method of claim 1, further comprising administering to the subject a composition which binds LT.

6. The method of claim 1, wherein the ETEC infection is travelers' diarrhea or infant diarrhea.

7. The method of claim 1, wherein the RBC preparation comprises whole erythrocytes, erythrocyte ghosts, erythrocyte fractions, erythrocyte extracts, glycolipid receptors isolated from erythrocytes, or combinations thereof.

8. A method of preventing, inhibiting, or reducing an amount of enterotoxigenic *Escherichia coli* (ETEC) adhering to a subject's intestinal wall comprising orally administering to the subject a therapeutically effective amount of a preparation containing isolated bovine red blood cell (RBC) and a carrier suitable for oral administration.

9. The method of claim 8, wherein the amount of ETEC adhering to the subject's intestinal wall is prevented, inhibited, or reduced by about 10% or greater.

10. The method of claim 8, wherein the amount of ETEC adhering to the subject's intestinal wall is prevented, inhibited, or reduced by greater than about 20%.

11. The method of claim 8, wherein the amount of ETEC adhering to the subject's intestinal wall is prevented, inhibited, or reduced by greater than about 30%.

12. The method of claim 8, wherein the amount of ETEC adhering to the subject's intestinal wall is prevented, inhibited, or reduced by greater than about 40%.

13. The method of claim 8, wherein the amount of ETEC adhering to the subject's intestinal wall is prevented, inhibited, or reduced by greater than about 50%.

* * * * *